United States Patent
Raman et al.

(10) Patent No.: US 9,289,298 B2
(45) Date of Patent: *Mar. 22, 2016

(54) METHOD AND APPARATUS FOR EXTERNAL STABILIZATION OF THE HEART

(71) Applicant: MARDIL, INC., Plymouth, MN (US)

(72) Inventors: JaiShankar Raman, Chicago, IL (US); P. Sriramo Rao, San Diego, CA (US)

(73) Assignee: Mardil, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/216,928

(22) Filed: Mar. 17, 2014

(65) Prior Publication Data

US 2014/0200397 A1    Jul. 17, 2014

Related U.S. Application Data

(63) Continuation of application No. 13/367,265, filed on Feb. 6, 2012, now Pat. No. 8,715,160, which is a continuation of application No. 11/637,286, filed on Dec. 12, 2006, now Pat. No. 8,128,553, which is a continuation of application No. 10/796,580, filed on Mar. 8, 2004, now Pat. No. 7,381,182, which is a continuation of application No. 10/236,640, filed on Sep. 6, 2002, now Pat. No. 6,716,158.

(60) Provisional application No. 60/318,172, filed on Sep. 7, 2001.

(51) Int. Cl.
*A61B 19/00*    (2006.01)
*A61F 2/24*    (2006.01)

(52) U.S. Cl.
CPC ............... *A61F 2/2481* (2013.01); *A61B 19/54* (2013.01)

(58) Field of Classification Search
CPC .......... A61F 2/2478; A61F 1/10; A61F 1/122
USPC ............... 600/16–1, 378, 16–18, 37; 607/129
See application file for complete search history.

(56) References Cited

U.S. PATENT DOCUMENTS

| | | |
|---|---|---|
| 963,899 A | 7/1910 | Kistler |
| 3,019,790 A | 2/1962 | Militana |
| 3,656,185 A | 4/1972 | Carpentier |
| 3,980,086 A | 9/1976 | Kletschka et al. |

(Continued)

FOREIGN PATENT DOCUMENTS

| | | |
|---|---|---|
| DE | 3227984 | 2/1984 |
| DE | 3614292 | 11/1987 |

(Continued)

OTHER PUBLICATIONS

ABIOMED, Inc. 1996 Annual Report, 32 pages.

(Continued)

*Primary Examiner* — John Lacyk
(74) *Attorney, Agent, or Firm* — Gordon Rees Scully Mansukhani LLP

(57) ABSTRACT

The present disclosure is directed to an external cardiac basal annuloplasty system (ECBAS or BACE-System: basal annuloplasty of the cardia externally) and methods for treatment of regurgitation of mitral and tricuspid valves. The BACE-System provides the ability to correct leakage of regurgitation of the valves with or without the use of cardiopulmonary bypass, particularly when the condition is related to dilation of the base of the heart. This ECBAS invention can be applied to the base of the heart epicardially, either to prevent further dilation or to actively reduce the size of the base of the heart.

19 Claims, 5 Drawing Sheets

(56) References Cited

U.S. PATENT DOCUMENTS

| | | |
|---|---|---|
| 3,983,863 A | 10/1976 | Janke et al. |
| 4,035,849 A | 7/1977 | Angell et al. |
| 4,048,990 A | 9/1977 | Goetz |
| 4,055,861 A | 11/1977 | Carpentier et al. |
| 4,192,293 A | 3/1980 | Asrican |
| 4,217,665 A | 8/1980 | Bex et al. |
| 4,261,342 A | 4/1981 | Aranguren Duo |
| 4,300,564 A | 11/1981 | Furihata |
| 4,306,319 A | 12/1981 | Kaster |
| 4,343,048 A | 8/1982 | Ross et al. |
| 4,372,293 A | 2/1983 | Vijil-Rosales |
| 4,403,604 A | 9/1983 | Wilkinson et al. |
| 4,409,974 A | 10/1983 | Freedland |
| 4,428,375 A | 1/1984 | Ellman |
| 4,536,893 A | 8/1985 | Parravicini |
| 4,579,120 A | 4/1986 | MacGregor |
| 4,592,342 A | 6/1986 | Salmasian |
| 4,629,459 A | 12/1986 | Ionescu et al. |
| 4,630,597 A | 12/1986 | Kantrowitz et al. |
| 4,632,101 A | 12/1986 | Freedland |
| 4,690,134 A | 9/1987 | Snyders |
| 4,705,040 A | 11/1987 | Mueller et al. |
| 4,821,723 A | 4/1989 | Baker, Jr. et al. |
| 4,878,890 A | 11/1989 | Bilweis |
| 4,936,857 A | 6/1990 | Kulik |
| 4,944,753 A | 7/1990 | Burgess et al. |
| 4,957,477 A | 9/1990 | Lundback |
| 4,960,424 A | 10/1990 | Grooters |
| 4,973,300 A | 11/1990 | Wright |
| 4,976,730 A | 12/1990 | Kwan-Gett |
| 4,991,578 A | 2/1991 | Cohen |
| 4,997,431 A | 3/1991 | Isner et al. |
| 5,057,117 A | 10/1991 | Atweh |
| 5,061,277 A | 10/1991 | Carpentier et al. |
| 5,087,243 A | 2/1992 | Avitall |
| 5,104,407 A | 4/1992 | Lam et al. |
| 5,106,386 A | 4/1992 | Isner et al. |
| 5,131,905 A | 7/1992 | Grooters |
| RE34,021 E | 8/1992 | Mueller et al. |
| 5,150,706 A | 9/1992 | Cox et al. |
| 5,152,765 A | 10/1992 | Ross et al. |
| 5,156,621 A | 10/1992 | Navia et al. |
| 5,169,381 A | 12/1992 | Snyders |
| 5,186,711 A | 2/1993 | Epstein |
| 5,192,314 A | 3/1993 | Daskalakis |
| 5,250,049 A | 10/1993 | Michael |
| 5,256,132 A | 10/1993 | Snyders |
| 5,258,015 A | 11/1993 | Li et al. |
| 5,284,488 A | 2/1994 | Sideris |
| 5,290,217 A | 3/1994 | Campos |
| 5,300,087 A | 4/1994 | Knoepfler |
| 5,312,642 A | 5/1994 | Chesterfield |
| 5,356,432 A | 10/1994 | Rutkow et al. |
| 5,360,444 A | 11/1994 | Kusuhara |
| 5,376,112 A | 12/1994 | Duran |
| 5,383,840 A | 1/1995 | Heilman et al. |
| 5,385,156 A | 1/1995 | Oliva |
| 5,385,528 A | 1/1995 | Wilk |
| 5,389,096 A | 2/1995 | Aita et al. |
| 5,397,331 A | 3/1995 | Himpens et al. |
| 5,417,709 A | 5/1995 | Slater |
| 5,429,584 A | 7/1995 | Chiu |
| 5,433,727 A | 7/1995 | Sideris |
| 5,445,600 A | 8/1995 | Abdulla |
| 5,450,860 A | 9/1995 | O'Connor |
| 5,452,733 A | 9/1995 | Sterman et al. |
| 5,458,574 A | 10/1995 | Machold et al. |
| 5,496,305 A | 3/1996 | Kittrell et al. |
| 5,507,779 A | 4/1996 | Altman |
| 5,509,428 A | 4/1996 | Dunlop |
| 5,522,884 A | 6/1996 | Wright |
| 5,524,633 A | 6/1996 | Heaven et al. |
| 5,533,958 A | 7/1996 | Wilk |
| 5,571,215 A | 11/1996 | Sterman et al. |
| 5,584,803 A | 12/1996 | Stevens et al. |
| 5,593,424 A | 1/1997 | Northrup III |
| 5,603,337 A | 2/1997 | Jarvik |
| 5,607,471 A | 3/1997 | Seguin et al. |
| 5,647,380 A | 7/1997 | Campbell et al. |
| 5,655,548 A | 8/1997 | Nelson et al. |
| 5,665,092 A | 9/1997 | Mangiardi et al. |
| 5,674,279 A | 10/1997 | Wright et al. |
| 5,682,906 A | 11/1997 | Sterman et al. |
| 5,702,343 A | 12/1997 | Alferness |
| 5,713,954 A | 2/1998 | Rosenberg et al. |
| 5,718,725 A | 2/1998 | Sterman et al. |
| 5,738,649 A | 4/1998 | Macoviak |
| 5,755,783 A | 5/1998 | Stobie et al. |
| 5,758,663 A | 6/1998 | Wilk et al. |
| 5,766,234 A | 6/1998 | Chen et al. |
| 5,776,189 A | 7/1998 | Khalid et al. |
| 5,800,334 A | 9/1998 | Wilk |
| 5,800,528 A | 9/1998 | Lederman et al. |
| 5,800,531 A | 9/1998 | Cosgrove et al. |
| 5,807,384 A | 9/1998 | Mueller |
| 5,814,097 A | 9/1998 | Sterman et al. |
| 5,824,066 A | 10/1998 | Gross |
| 5,824,069 A | 10/1998 | Lemole |
| 5,840,059 A | 11/1998 | March et al. |
| 5,849,005 A | 12/1998 | Garrison et al. |
| 5,855,601 A | 1/1999 | Bessler et al. |
| 5,855,614 A | 1/1999 | Stevens et al. |
| 5,865,791 A | 2/1999 | Whayne et al. |
| 5,876,436 A | 3/1999 | Vanney et al. |
| 5,888,240 A | 3/1999 | Carpentier et al. |
| 5,902,229 A | 5/1999 | Tsitlik et al. |
| 5,928,281 A | 7/1999 | Huynh et al. |
| 5,944,738 A | 8/1999 | Amplatz et al. |
| 5,957,977 A | 9/1999 | Melvin |
| 5,961,440 A | 10/1999 | Schweich, Jr. et al. |
| 5,961,539 A | 10/1999 | Northrup, III et al. |
| 5,961,549 A | 10/1999 | Nguyen et al. |
| 5,967,990 A | 10/1999 | Thierman et al. |
| 5,971,910 A | 10/1999 | Tsitlik et al. |
| 5,971,911 A | 10/1999 | Wilk |
| 5,972,022 A | 10/1999 | Huxel |
| 5,972,030 A | 10/1999 | Garrison et al. |
| 5,976,551 A | 11/1999 | Mottez et al. |
| 5,984,857 A | 11/1999 | Buck et al. |
| 5,984,917 A | 11/1999 | Fleischman et al. |
| 5,999,678 A | 12/1999 | Murphy-Chutorian et al. |
| 6,001,126 A | 12/1999 | Nguyen-Thien-Nhon |
| 6,019,722 A | 2/2000 | Spence et al. |
| 6,024,096 A | 2/2000 | Buckberg |
| 6,024,756 A | 2/2000 | Huebsch et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,086,532 A | 7/2000 | Panescu et al. |
| 6,095,968 A | 8/2000 | Snyders |
| 6,102,944 A | 8/2000 | Huynh et al. |
| 6,110,100 A | 8/2000 | Talpade |
| 6,113,536 A | 9/2000 | Aboul-Hosn et al. |
| 6,117,159 A | 9/2000 | Huebsch et al. |
| 6,120,520 A | 9/2000 | Saadat et al. |
| 6,123,662 A | 9/2000 | Alferness |
| 6,125,852 A | 10/2000 | Stevens et al. |
| 6,126,590 A | 10/2000 | Alferness |
| 6,129,758 A | 10/2000 | Love |
| 6,132,438 A | 10/2000 | Fleischman et al. |
| 6,143,025 A | 11/2000 | Stobie et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,165,183 A | 12/2000 | Kuehn et al. |

(56) References Cited

U.S. PATENT DOCUMENTS

| | | |
|---|---|---|
| 6,169,922 B1 | 1/2001 | Alferness et al. |
| 6,174,279 B1 | 1/2001 | Girard |
| 6,174,332 B1 | 1/2001 | Loch et al. |
| 6,179,791 B1 | 1/2001 | Krueger |
| 6,182,664 B1 | 2/2001 | Cosgrove |
| 6,183,411 B1 | 2/2001 | Mortier et al. |
| 6,190,408 B1 | 2/2001 | Melvin |
| 6,193,646 B1 | 2/2001 | Kulisz et al. |
| 6,197,053 B1 | 3/2001 | Cosgrove et al. |
| 6,206,004 B1 | 3/2001 | Schmidt et al. |
| 6,206,820 B1 | 3/2001 | Kazi |
| 6,217,610 B1 | 4/2001 | Carpentier et al. |
| 6,221,013 B1 | 4/2001 | Panescu et al. |
| 6,221,103 B1 | 4/2001 | Melvin |
| 6,221,104 B1 | 4/2001 | Buckberg et al. |
| 6,224,540 B1 | 5/2001 | Lederman et al. |
| 6,230,714 B1 | 5/2001 | Alferness et al. |
| 6,231,518 B1 | 5/2001 | Grabek et al. |
| 6,238,334 B1 | 5/2001 | Easterbrook, III et al. |
| 6,241,654 B1 | 6/2001 | Alferness |
| 6,245,102 B1 | 6/2001 | Jayaraman |
| 6,245,105 B1 | 6/2001 | Nguyen et al. |
| 6,250,308 B1 | 6/2001 | Cox |
| 6,251,061 B1 | 6/2001 | Hastings et al. |
| 6,258,021 B1 | 7/2001 | Wilk |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,269,819 B1 | 8/2001 | Oz et al. |
| 6,283,993 B1 | 9/2001 | Cosgrove et al. |
| 6,293,906 B1 | 9/2001 | Vanden Hoek et al. |
| 6,309,370 B1 | 10/2001 | Haim et al. |
| 6,314,322 B1 | 11/2001 | Rosenberg |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,338,712 B2 | 1/2002 | Spence et al. |
| 6,360,749 B1 | 3/2002 | Jayaraman |
| 6,361,545 B1 | 3/2002 | Macoviak et al. |
| 6,370,429 B1 | 4/2002 | Alferness et al. |
| 6,375,608 B1 | 4/2002 | Alferness |
| 6,379,366 B1 | 4/2002 | Fleischman et al. |
| 6,391,054 B2 | 5/2002 | Carpentier et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,432,059 B2 | 8/2002 | Hickey |
| 6,439,237 B1 | 8/2002 | Buckberg et al. |
| 6,443,949 B2 | 9/2002 | Altman |
| 6,450,171 B1 | 9/2002 | Buckberg et al. |
| 6,461,366 B1 | 10/2002 | Seguin |
| 6,482,146 B1 | 11/2002 | Alferness et al. |
| 6,488,618 B1 | 12/2002 | Paolitto et al. |
| 6,488,706 B1 | 12/2002 | Solymar |
| 6,494,825 B1 | 12/2002 | Talpade |
| 6,508,756 B1 | 1/2003 | Kung et al. |
| 6,511,426 B1 | 1/2003 | Hossack et al. |
| 6,514,194 B2 | 2/2003 | Schweich, Jr. et al. |
| 6,520,904 B1 | 2/2003 | Melvin |
| 6,537,198 B1 | 3/2003 | Vidlund et al. |
| 6,537,203 B1 | 3/2003 | Alferness et al. |
| 6,544,167 B2 | 4/2003 | Buckberg et al. |
| 6,544,168 B2 | 4/2003 | Alferness |
| 6,544,180 B1 | 4/2003 | Doten et al. |
| 6,547,716 B1 | 4/2003 | Milbocker |
| 6,547,821 B1 | 4/2003 | Taylor et al. |
| 6,558,319 B1 | 5/2003 | Aboul-Hosn et al. |
| 6,564,094 B2 | 5/2003 | Alferness et al. |
| 6,565,511 B2 | 5/2003 | Panescu et al. |
| 6,567,699 B2 | 5/2003 | Alferness et al. |
| 6,569,082 B1 | 5/2003 | Chin |
| 6,572,529 B2 | 6/2003 | Wilk |
| 6,572,533 B1 | 6/2003 | Shapland et al. |
| 6,575,921 B2 | 6/2003 | Vanden Hoek et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi et al. |
| 6,589,160 B2 | 7/2003 | Schweich, Jr. et al. |
| 6,592,514 B2 | 7/2003 | Kolata et al. |
| 6,592,619 B2 | 7/2003 | Melvin |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,622,730 B2 | 9/2003 | Ekvall et al. |
| 6,629,921 B1 | 10/2003 | Schweich, Jr. et al. |
| 6,645,139 B2 | 11/2003 | Haindl |
| 6,651,671 B1 | 11/2003 | Donlon et al. |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,627 B2 | 2/2004 | Jayaraman |
| 6,685,646 B2 | 2/2004 | Cespedes et al. |
| 6,689,048 B2 | 2/2004 | Vanden Hoek et al. |
| 6,695,768 B1 | 2/2004 | Levine et al. |
| 6,695,769 B2 | 2/2004 | French et al. |
| 6,695,866 B1 | 2/2004 | Kuehn et al. |
| 6,701,929 B2 | 3/2004 | Hussein |
| 6,702,732 B1 | 3/2004 | Lau et al. |
| 6,709,382 B1 | 3/2004 | Horner |
| 6,716,158 B2 | 4/2004 | Raman et al. |
| 6,723,038 B1 | 4/2004 | Schroeder et al. |
| 6,723,041 B2 | 4/2004 | Lau et al. |
| 6,726,696 B1 | 4/2004 | Houser |
| 6,726,920 B1 | 4/2004 | Theeuwes et al. |
| 6,730,016 B1 * | 5/2004 | Cox et al. .................. 600/37 |
| 6,746,471 B2 | 6/2004 | Mortier et al. |
| 6,755,777 B2 | 6/2004 | Schweich, Jr. et al. |
| 6,755,779 B2 | 6/2004 | Vanden Hoek et al. |
| 6,755,861 B2 | 6/2004 | Nakao |
| 6,764,510 B2 | 7/2004 | Vidlund et al. |
| 6,776,754 B1 | 8/2004 | Wilk |
| 6,793,618 B2 | 9/2004 | Schweich, Jr. et al. |
| 6,808,488 B2 | 10/2004 | Mortier et al. |
| 6,814,700 B1 | 11/2004 | Mueller et al. |
| 6,830,576 B2 | 12/2004 | Fleischman et al. |
| 6,837,247 B2 | 1/2005 | Buckberg et al. |
| 6,852,075 B1 | 2/2005 | Taylor |
| 6,852,076 B2 | 2/2005 | Nikolic et al. |
| 6,858,001 B1 | 2/2005 | Aboul-Hosn |
| 6,876,887 B2 | 4/2005 | Okuzumi et al. |
| 6,881,185 B2 | 4/2005 | Vanden Hock et al. |
| 6,893,392 B2 | 5/2005 | Alferness |
| 6,896,652 B2 | 5/2005 | Alferness et al. |
| 6,902,523 B2 | 6/2005 | Kochamba |
| 6,908,424 B2 | 6/2005 | Mortier et al. |
| 6,936,002 B2 | 8/2005 | Kochamba et al. |
| 6,984,201 B2 | 1/2006 | Asgher et al. |
| 6,997,865 B2 | 2/2006 | Alferness et al. |
| 7,022,063 B2 | 4/2006 | Lau et al. |
| 7,022,064 B2 | 4/2006 | Alferness et al. |
| 7,025,719 B2 | 4/2006 | Alferness et al. |
| 7,044,905 B2 | 5/2006 | Vidlund et al. |
| 7,056,280 B2 | 6/2006 | Buckberg et al. |
| 7,060,021 B1 | 6/2006 | Wilk |
| 7,077,862 B2 | 7/2006 | Vidlund et al. |
| 7,097,611 B2 | 8/2006 | Lau et al. |
| 7,112,219 B2 | 9/2006 | Vidlund et al. |
| 7,153,258 B2 | 12/2006 | Alferness et al. |
| 7,163,507 B2 | 1/2007 | Alferness |
| 7,166,071 B2 | 1/2007 | Alferness |
| 7,186,210 B2 | 3/2007 | Feld et al. |
| 7,189,199 B2 | 3/2007 | McCarthy et al. |
| 7,229,402 B2 | 6/2007 | Diaz et al. |
| 7,235,042 B2 | 6/2007 | Vanden Hoek et al. |
| 7,255,674 B2 | 8/2007 | Alferness |

(56) References Cited

U.S. PATENT DOCUMENTS

| | | | |
|---|---|---|---|
| 7,261,684 B2 | 8/2007 | Alferness |
| 7,274,962 B2 | 9/2007 | Bardy et al. |
| 7,275,546 B2 | 10/2007 | Buckberg et al. |
| 7,278,964 B2 | 10/2007 | Alferness |
| 7,291,105 B2 | 11/2007 | Lau et al. |
| 7,326,174 B2 | 2/2008 | Cox et al. |
| 7,351,200 B2 | 4/2008 | Alferness |
| 7,361,137 B2 | 4/2008 | Taylor et al. |
| 7,361,191 B2 | 4/2008 | Lau et al. |
| 7,381,181 B2 | 6/2008 | Lau et al. |
| 7,381,182 B2 | 6/2008 | Raman et al. |
| 7,390,293 B2 | 6/2008 | Jayaraman |
| 7,410,461 B2 | 8/2008 | Lau et al. |
| 7,464,712 B2 | 12/2008 | Oz et al. |
| 7,485,090 B2 | 2/2009 | Taylor |
| 7,572,219 B2 | 8/2009 | Lau et al. |
| 7,575,547 B2 | 8/2009 | Alferness et al. |
| 7,578,784 B2 | 8/2009 | Alferness et al. |
| 7,651,461 B2 | 1/2010 | Alferness et al. |
| 7,682,305 B2 | 3/2010 | Bertolero et al. |
| 7,695,425 B2 | 4/2010 | Schweich et al. |
| 7,722,523 B2 | 5/2010 | Mortier et al. |
| 7,758,494 B2 | 7/2010 | Buckberg et al. |
| 7,758,596 B2 | 7/2010 | Oz et al. |
| 7,883,539 B2 | 2/2011 | Schweich, Jr. et al. |
| 8,128,553 B2 * | 3/2012 | Raman et al. ................ 600/37 |
| 8,187,323 B2 | 5/2012 | Mortier et al. |
| 8,226,711 B2 | 7/2012 | Mortier et al. |
| 2001/0029314 A1 | 10/2001 | Alferness et al. |
| 2002/0022880 A1 | 2/2002 | Melvin |
| 2002/0029783 A1 | 3/2002 | Stevens et al. |
| 2002/0065449 A1 | 5/2002 | Wardle |
| 2002/0065465 A1 | 5/2002 | Panescu et al. |
| 2002/0077524 A1 | 6/2002 | Schweich, Jr. et al. |
| 2002/0111533 A1 | 8/2002 | Melvin |
| 2002/0147406 A1 | 10/2002 | Von Segesser |
| 2003/0045771 A1 | 3/2003 | Schweich, Jr. et al. |
| 2003/0105519 A1 | 6/2003 | Fasol et al. |
| 2003/0181928 A1 | 9/2003 | Vidlund et al. |
| 2004/0059181 A1 | 3/2004 | Alferness |
| 2004/0102678 A1 | 5/2004 | Haindl |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0167539 A1 | 8/2004 | Kuehn et al. |
| 2004/0181125 A1 | 9/2004 | Alferness et al. |
| 2004/0225304 A1 | 11/2004 | Vidlund et al. |
| 2004/0249242 A1 | 12/2004 | Lau et al. |
| 2004/0267083 A1 | 12/2004 | McCarthy et al. |
| 2005/0058853 A1 | 3/2005 | Kochamba |
| 2005/0065396 A1 | 3/2005 | Mortier et al. |
| 2005/0075723 A1 | 4/2005 | Schroeder et al. |
| 2005/0085688 A1 | 4/2005 | Girard et al. |
| 2006/0009842 A1 | 1/2006 | Huynh et al. |
| 2006/0063970 A1 | 3/2006 | Raman et al. |
| 2006/0161040 A1 | 7/2006 | McCarthy et al. |
| 2006/0195012 A1 | 8/2006 | Mortier et al. |
| 2007/0004962 A1 | 1/2007 | Alferness et al. |
| 2007/0112244 A1 | 5/2007 | McCarthy et al. |
| 2007/0225547 A1 | 9/2007 | Alferness |

FOREIGN PATENT DOCUMENTS

| | | |
|---|---|---|
| DE | 4234127 | 5/1994 |
| DE | 29500381 | 7/1995 |
| DE | 29619294 | 7/1997 |
| DE | 29824017 | 6/1998 |
| DE | 19826675 | 3/1999 |
| DE | 19947885 | 4/2000 |
| EP | 0583012 | 2/1994 |
| EP | 0792621 | 9/1997 |
| EP | 0820729 | 1/1998 |
| GB | 2214428 | 9/1989 |
| NL | 9200878 | 12/1993 |
| WO | WO 9119465 | 12/1991 |
| WO | WO 9506447 | 3/1995 |
| WO | WO 9516407 | 6/1995 |
| WO | WO 9516476 | 6/1995 |
| WO | WO 9602197 | 2/1996 |
| WO | WO 9604852 | 2/1996 |
| WO | WO 9640356 | 12/1996 |
| WO | WO 9714286 | 4/1997 |
| WO | WO 9724082 | 7/1997 |
| WO | WO 9724083 | 7/1997 |
| WO | WO 9724101 | 7/1997 |
| WO | WO 9741779 | 11/1997 |
| WO | WO 9803213 | 1/1998 |
| WO | WO 98/14136 * | 4/1998 |
| WO | WO 9814136 | 4/1998 |
| WO | WO 9817347 | 4/1998 |
| WO | WO 9818393 | 5/1998 |
| WO | WO 9826738 | 6/1998 |
| WO | WO 9829041 | 7/1998 |
| WO | WO 9832382 | 7/1998 |
| WO | WO 9844969 | 10/1998 |
| WO | WO 9858598 | 12/1998 |
| WO | WO 9900059 | 12/1998 |
| WO | WO 9911201 | 3/1999 |
| WO | WO 9913777 | 3/1999 |
| WO | WO 9913936 | 3/1999 |
| WO | WO 9916350 | 4/1999 |
| WO | WO 9922784 | 5/1999 |
| WO | WO 9930647 | 6/1999 |
| WO | WO 9944534 | 9/1999 |
| WO | WO 9944680 | 9/1999 |
| WO | WO 9952470 | 10/1999 |
| WO | WO 9952471 | 10/1999 |
| WO | WO 9953977 | 10/1999 |
| WO | WO 9956655 | 11/1999 |
| WO | WO 9966969 | 12/1999 |
| WO | WO 0002500 | 1/2000 |
| WO | WO 0003759 | 1/2000 |
| WO | WO 0006026 | 2/2000 |
| WO | WO 0006028 | 2/2000 |
| WO | WO 0013722 | 3/2000 |
| WO | WO 0018320 | 4/2000 |
| WO | WO 0025842 | 5/2000 |
| WO | WO 0025853 | 5/2000 |
| WO | WO 0027304 | 5/2000 |
| WO | WO 0028912 | 5/2000 |
| WO | WO 0028918 | 5/2000 |
| WO | WO 0036995 | 6/2000 |
| WO | WO 0042919 | 7/2000 |
| WO | WO 0045735 | 8/2000 |
| WO | WO 0061033 | 10/2000 |
| WO | WO 0062727 | 10/2000 |
| WO | WO 0103608 | 1/2001 |
| WO | WO 0110421 | 2/2001 |
| WO | WO 0121070 | 3/2001 |
| WO | WO 0121098 | 3/2001 |
| WO | WO 0121099 | 3/2001 |
| WO | WO 0150981 | 7/2001 |
| WO | WO 0191667 | 12/2001 |
| WO | WO 0195830 | 12/2001 |
| WO | WO 0200099 | 1/2002 |
| WO | WO 0213726 | 2/2002 |
| WO | WO 03022131 | 3/2003 |

OTHER PUBLICATIONS

Alonso-Lej, M.D., "Adjustable Annuloplasty for Tricuspid Insufficiency," The Annals of Thoracic Surgery, vol. 46, No. 3, Sep. 1988, 2 pages.

Alonso-Lej, The Journal of Thoracic and Cardiovascular Surgery, vol. 68, No. 3, Sep. 1974, p. 349.

Batch et al., "Early Improvement in Congestive Heart Failure after Correction of Secondary Mitral Regurgitation in End-Stage Cardiomyopathy," American Heart Journal, Jun. 1995, pp. 1165-1170.

Bailey et al., "Closed Intracardiac Tactile Surgery", Diseases of the Chest, 1952, XXII:1-24.

(56) References Cited

OTHER PUBLICATIONS

Bailey et al., "The Surgical Correction of Mitral Insufficiency by the Use of Pericardial Grafts", The Journal of Thoracic Surgery, 1954, 28:(6):551-603.
Batista et al., "Partial Left Ventriculectomy to Improve Left Ventricular Function in End-Stage Heart Disease," J. Card. Surg., 1996:11:96-98.
Batista, MD et al., "Partial Left Ventriculectomy to Treat End-Stage Heart Disease", Ann. Thorac. Surg., 64:634-8, 1997.
Bearnson et al., "Development of a Prototype Magnetically Suspended Rotor Ventricular Assist Device," ASAIO Journal, 1996, pp. 275-280.
Bocchi et al., "Clinical Outcome after Surgical Remodeling of Left Ventricle in Candidates to Heart Transplantation with Idiopathic Dilated Cardiomyopathy—Short Term Results," date even with or prior to Jan. 2, 1997, 1 page.
Bolling et al., "Surgery for Acquired Heart Disease/Early Outcome of Mitral Valve Reconstruction in Patients with End-Stage Cardiomyopathy," The Journal of Thoracic and Cardiovascular Surgery. vol. 109. No. 4. Apr. 1995. pp. 676-683.
Bolling, et al., "Intermediate-term Outcome of Mitral Reconstruction in Cardiomyopathy", J. Thorac. Cardiovasc. Surg. Feb. 1998, vol. 115, No. 2, pp. 381-388.
Bourge, "Clinical Trial Begins for Innovative Device-Altering Left Ventricular Shape in Heart Failure," UAB Insight, Aug. 8, 2002.
Boyd et al., "Tricuspid Annuloplasty," The Journal of Thoracic Cardiovascular Surgery. vol. 68, No. 3, Sep. 1974, 8 pages.
Brochure entitled "Thoratec Ventricular Assist Device System—Because Heart Patients Come in All Sizes," date even with or prior to Jan. 2, 1997, 5 pages.
Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997. pp. 626-628.
Carpentier et al., "Myocardial Substitution with a Stimulated Skeletal Muscle: First Successful Clinical Case," Letter to the Editor. Lancet 1:1267, Sep. 25, 1996.
Chachques et al., "Latissimus Dorsi Dynamic Cardiomyoplasty," Ann. Thorac. Surg., 1989:47:600-604.
Congestive Heart Failure in the United States: A New Epidemic Data Fact Sheet, National Heart, Lung, and Blood Institute, National Institutes of Health, Dec. 9, 1996, pp. 1-6.
Cox, "Left Ventricular Aneurysms: Pathophysiologic Observations and Standard Resection," Seminars in Thoracic and Cardiovascular Surgery, vol. 9, No. 2, Apr. 1997, pp. 113-122.
Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997. pp. 632-636.
Dickstein et al., "Heart Reduction Surgery: An Analysis of the Impact on Cardiac Function," The Journal of Thoracic and Cardiovascular Surgery, vol. 113, No. 6, Jun. 1997, 9 pages.
Doty M.D., "Septation of the Univentricular Heart," The Journal of Thoracic and Cardiovascular Surgery, vol. 78, No. 3, Sep. 1979, pp. 423-430.
Edie, M.D. et al., "Surgical Repair of Single Ventricle," The Journal of Thoracic and Cardiovascular Surgery, vol. 66, No. 3, Sep. 1973, pp. 350-360.
Farrar et al., "A New Skeletal Muscle Linear-Pull Energy Convertor as a Power Source for Prosthetic Support Devices," The Journal of Heart & Lung Transplantation, vol. 11, No. 5, Sep. 1992, pp. 341-349.
Feldt, M. D., "Current Status of the Septation Procedure for Univentricular Heart," The Journal of Thoracic and Cardiovascular Surgery, vol. 82, No. 1, Jul. 1981, pp. 93-97.
Glenn et al., "The Surgical Treatment of Mitral Insufficiency: The Fate of a Vascularized Transchamber Intracardiac Graft", Annals of Surgery, 1955, 141 :4:510-518.

Harken et al., "The Surgical Correction of Mitral Insufficiency", The Journal of Thoracic Surgery, 1954, 28:604627.
Harken et al., "The Surgical Correction of MitralInsufficency", Surgical Forum, 1953, 4:4-7.
Hayden et al., "Scintiphotographic Studies of Acquired Cardiovascular Disease," Seminars in Nuclear Medicine, vol. III, No. 2, Apr. 1973, pp. 177-190.
Huikuri, "Effect of Mitral.Valve Replacement on Left Ventricular Function in Mitral Regurgitation," Br. Heart J., vol. 49, 1983, pp. 328-333.
Kay et al., "Surgical Treatment of Mitral Insufficiency", Surgery, 1955, 37:(5):697-706.
Kay et al., "Surgical Treatment of Mitral Insufficiency", The Journal of Thoracic Surgery, 1955, 29:618-620.
Kormos et al., "Experience with Univentricular Support in Mortally Ill Cardiac Transplant Candidates," Ann. Thorac. Surg., 1990:49:261-71.
Kurlansky et al., "Adjustable Annuloplasty for Tricuspid Insufficiency," Ann. Thorac. Surg., 44:404-406, Oct. 1987.
Lamas, et al., "Clinical Significance of Mitral Regurgitation After Acute Myocardial Infarction", Circulation Aug. 5, 1997, vol. 96, No. 3, pp. 96-827, 827-833.
Ianuzzo et al., "Preservation of the Latissimus Dorsi Muscle During Cardiomyoplasty Surgery," J. Card. Surg., 1996:11:99-108.
Ianuzzo et al., "On Preconditioning of Skeletal Muscle: Application to Dynamic Cardiomyoplasty," Invited Commentary, J. Card. Surg., 1996:11:109-110.
Lei-Cohen, et al., "Design of a New Surgical Approach for Ventricular Remodeling to Relieve Ischemic Mitral Regurgitation", Circulation Jun. 13, 2000, vol. 101, pp. 2756-2763.
Lev, M.D., et al., "Single (Primitive) Ventricle," Circulation, vol. 39, May 1969, pp. 577-591.
Lucas et al., "Long-Term Follow-Up (12 to 35 Weeks) After Dynamic Cardiomyoplasty," JACC, vol. 22, No. 3, Sep. 1993:758-67.
Masahiro et al., "Surgery for Acquired Heart Disease/Effects of Preserving Mitral Apparatus on Ventricular Systolic Function in Mitral Valve Operations in Dogs," The Journal of Thoracic and Cardiovascular Surgery. vol. 106, No. 6, Dec. 1993, pp. 1138-1146.
McCarthy et al., "Clinical Experience with the Novacor Ventricular Assist System," J. Thorac. Cardiovasc. Surg., 1991:102:578-87.
McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.
McGoon, M.D. et al., "Correction of the Univentricular Heart Having Two Atrioventricular ValVes," The Journal of Thoracic and Cardiovascular Surgery, vol. 74, No. 2, Aug. 1977, pp. 218-226.
Medtronic, Inc. 1996 Annual Shareholders Report, 79 pages.
Melvin DB et al., "Reduction of Ventricular Wall Tensile Stress by Geometric Remodeling Device", Poster text ASAIO 1999.
Melvin, D.B. "Ventricular Radius Reduction Without Resection: A Computational Assessment," ASAIO Journal (Abstract), vol. 44, No. 2, pp. 57A, Mar. 5, 1998.
Melvin, Ventricular Radius Reduction Without Resection: A Computational Analysis, ASAIO Journal, 45:160-165, 1999.
Moreira et al., "Latissimus Dorsi Cardiomyoplasty in the Treatment of Patients with Dilated Cardiomyopathy," Circulation, 1990;82(5 Suppl.):IV 257-63.
Pai, et al., "Prognostic Importance of Mitral Regurgitation at All Levels of LV Systolic Function: Results from a Cohort of 8931 Patients," Circulation, 2000, vol. 102, No. 18, p. 11-369.
Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.
Pitarys II et al., "Long-Term Effects of Excision of the Mitral Apparatus on Global and Regional Ventricular Function in Humans," JACC, vol. 15, No. 3, Mar. 1, 1990, pp. 557-563.
Press Release dated Apr. 27, 1995, "ABIOMED's Temporary Artificial Heart System Reaches 1,000 Patient Milestone; BVS-5000 in More Than 100 U.S. Medical Centers," 1 page.

(56) References Cited

OTHER PUBLICATIONS

Press Release dated Aug. 11, 1995, "ABIOMED Receives Grant from NIH to Develop Disposable Bearingless Centrifugal Blood Pump," 1 page.
Press Release dated Aug. 25, 1995, "ABIOMED Wins Research Grant from NIH to Develop Suturing Instrument for Abdominal Surgery," 1 page.
Press Release dated Jun. 9, 1995, "ABIOMED Receives Grant from National Institutes of Health to Develop a Laser Welding Technique for Tissue Repair," 1 page.
Press Release dated May 17, 1996, "ABIOMED Receives FDA Approval to Expand Indications for Use of Cardiac Assist System," 1 page.
Press Release dated Oct. 3, 1994, "Heartmate System Becomes First Implantable Cardiac-Assist Device to be Approved for Commercial Sale in the U.S.," 2 pages.
Press Release dated Oct. 3, 1995, "ABIOMED Wins $4.35 Million Contract from the National Heart, Lung and Blood Institutes to Develop Implantable Heart Booster," 1 page.
Press Release dated Sep. 16, 1996, "ABIOMED Wins $8.5 Million Federal Contract to Qualify its Artificial Heart for Human Trials," 5 pages.
Press Release dated Sep. 26, 1996, "ABIOMED's Temporary Artificial Heart System Reaches 200 U.S. Medical Center Milestone," 1 page.
Press Release dated Sep. 29, 1995, "ABIOMED" Wins NIH Grant to Develop Calcification-Resistant Plastic Heart Valve, 1 page.
Reversible Cardiomyopathy, Thoratec's Heartbeat, vol. 10.2, Aug. 1996, 4 pages.
Sakakibara et al., "A Muscle Powered Cardiac Assist Device for Right Ventricular Support: Total Assist or Partial Assist?," Trans. Am. Soc. Artif. Intern. Organs, vol. XXXVI, 1990, pp. 372-375.
Sakakibara, "A Surgical Approach to the Correction of Mitral Insufficiency", Annals of Surgery, 1955, 142:196203.
Savage, M.D., "Repair of Left Ventricular Aneurysm," The Journal of Thoracic and Cardiovascular Surgery, vol. 104, No. 3, Sep. 1992, pp. 752-762.
Schuler et al., "Temporal Response of Left Ventricular Performance to Mitral Valve Surgery," vol. 59, No. 6, Jun. 1979, pp. 1218-1231.
Shumacker, "Cardiac Aneurysms," The Evolution of Cardiac Surgery, 1992, pp. 159-165.
Shumacker, Jr., "Attempts to Control Mitral Regurgitation", The Evolution of Cardiac Surgery, 1992, 203-210.
Timek, et al., "Pathogenesis of Mitral Regurgitation in Tachycardia Induced Cardiomyapathy," Circulation, Oct. 31, 2000, vol. 102, No. 18, p. 11-420.
Tsai et al., "Surface Modifying Additives for Improved Device-Blood Compatibility," ASIAO Journal, 1994, pp. 619-624.
Wampler et al., "Treatment of Cardiogenic Shock with the Hemopump Left Ventricular Assist Device," Ann. Thorac. Surg., 1991:52:506-13.
Westaby with Bosher, "Landmarks in Cardiac Surgery," 1997, pp. 198-199.

\* cited by examiner

METHOD AND APPARATUS FOR EXTERNAL STABILIZATION OF THE HEART

CROSS REFERENCE TO RELATED APPLICATION

This application is a continuation of U.S. patent application Ser. No. 13/367,265 filed Feb. 6, 2012, now U.S. Pat. No. 8,715,160 issued May 6, 2014, which is a continuation of U.S. patent application Ser. No. 11/637,286 filed Dec. 12, 2006, now U.S. Pat. No. 8,128,553 issued Mar. 6, 2012, which is a continuation U.S. patent application Ser. No. 10/796,580 filed Mar. 8, 2004, now U.S. Pat. No. 7,381,182 issued Jun 3, 2008, which is a continuation of U.S. patent application Ser. No. 10/236,640 filed Sep. 6, 2002, now U.S. Pat. No. 6,716,158 issued Apr. 6, 2004, which claims the benefit of U.S. Provisional Application No. 60/318,172 filed Sep. 7, 2001. The contents of each of these prior applications are incorporated herein by reference in their entirety.

FIELD OF THE INVENTION

The present invention relates to devices and methods for treating dilatation of the valves at the base of the heart by external stabilization of the base of the heart, which subtend the atrio-ventricular valves of the heart.

BACKGROUND OF THE INVENTION

Dilatation of the base of the heart occurs with various diseases of the heart and often is a causative mechanism of heart failure. In some instances, depending on the cause, the dilatation may be localized to one portion of the base of the heart (e.g., mitral insufficiency as a consequence of a heart attack affecting the inferior and basal wall of the left ventricle of the heart), thereby affecting the valve in that region. In other cases, such as cardiomyopathy, the condition may be global affecting more of the heart and its base, causing leakage of particularly the mitral and tricuspid valves. Other conditions exist where the mitral valve structure is abnormal, predisposing to leakage and progressive dilatation of the valve annulus (area of valve attachment to the heart). This reduces the amount of blood being pumped out by the ventricles of the heart, thereby impairing cardiac function further.

In patients with heart failure and severe mitral insufficiency, good results have been achieved by aggressively repairing mitral and/or tricuspid valves directly, which requires open-heart surgery (Bolling, et al.). The mitral valve annulus is reinforced internally by a variety of prosthetic rings (Duran Ring, Medtronic Inc) or bands (Cosgrove-Edwards Annuloplasty Band, Edwards Lifesciences Inc). The present paradigm of mitral valve reconstruction is therefore repair from inside the heart, with the annulus being buttressed or reinforced by the implantation of a prosthetic-band or ring. Since this is major open-heart surgery with intra-cavitary reconstruction, there is the attendant risk of complications and death associated with mitral valve surgery. Another approach has been to replace the mitral valve, which while addressing the problem, also requires open-heart surgery and involves implantation of a bulky artificial, prosthetic valve with all its consequences. Because every decision to perform major surgery requires some risk vs. benefit consideration, patients get referred for risky surgery only when they are significantly symptomatic or their mitral valve is leaking severely.

In contrast to the more invasive approaches discussed above, in specific instances of inferior left ventricular wall scarring causing mitral regurgitation, Levine and co-workers have suggested localized pressure or support of the bulging scar of the inferior wall of the heart from the outside.

Another less invasive approach to preventing global heart dilation is ventricular containment with a custom made polyester mesh, or cardiac support device (U.S. Pat. Nos. 6,077,218 and 6,123,662). These devices are designed to provide a passive constraint around both ventricles of the heart, and constrain diastolic expansion of the heart. Other devices include ventricular assist devices that provide cardiac assistance during systole and dynamic ventricular reduction devices that actively reduce the size of the heart. However, this technique does not specifically address valve leakage using a device that reinforces the base of the heart in all phases of the cardiac cycle.

Accordingly, there is a need to provide a less invasive, simple technique of repairing, reinforcing, reducing or stabilizing the base of the heart and its underlying valves (mitral and tricuspid valves) from the outside.

SUMMARY OF THE INVENTION

The present invention addresses the problems discussed above by providing a device for the treatment of certain heart disorders, in particular mitral and/or tricuspid valve insufficiency. The device aims to reduce the size of the base of the heart that contains these valvular structures. In addition, the present invention can be used to address progressive dilatation of any localized area of the heart, such as the atrial or ventricular myocardium, or the cardiac base. It does so by providing external re-enforcement or remodeling of the cardiac base. As used herein, the surgical procedure for implanting the device is referred to as basal annuloplasty of the cardia externally ("BACE") and the device is referred to as the external cardiac basal annuloplasty system ("ECBAS") or BASE System.

In one embodiment, a customized or specially constructed biocompatible strip is implanted along the base of the heart at the level of the atrio-ventricular groove. The strip or mesh is between 2 and 5 cm wide and is secured by 2 rows of clips or sutures, one on the atrial side and the other on the ventricular side of the atrio-ventricular groove. Specific care is taken to avoid injury to the circumflex and right coronary arteries and the coronary sinus. This procedure may be performed either as a stand-alone procedure or as an adjunct to other cardiac surgery. Additionally, it may be performed with or without the aid of cardio-pulmonary bypass.

Another embodiment of this approach is a device or strip, which once implanted at a certain size, can be tightened over time either by inflation of an attached chamber or programmed to return to a pre-formed size (based on elasticity or pre-existing memory) of the material used.

Another embodiment of this device, while externally stabilizing the base of the heart, also provides a localized increase in contraction along any segment of the base to improve contractile function. This may be accomplished by the aid of contractile metal or modified muscle or other cells.

Variations of the device include a complete stabilization of the base of the heart, or a partial stabilization around the expansible portions of the mitral and tricuspid valves by a biocompatible strip.

Another variation seeks to use ports along the device that will facilitate delivery of specialized drugs, gene therapeutic agents, growth factors, etc.

A specific variation incorporates the use of epicardial bi-ventricular pacing electrodes implanted along with the BACE-Sys, where multi-site pacing might be indicated.

The invention also provides a method of implantation, which may be through a conventional full median sternotomy with the strip being secured by sutures, or a minimally invasive approach whereby the device/strip may be implanted by a specialized implantation system using adhesives, self-firing clips, sutures, etc.

Another modification of this technique is the local application of prosthetic material to stabilize scars of the heart to prevent their expansion (local ventricular stabilization).

In an alternate embodiment, the device incorporates additional strips to be used in concert or as an extension to provide localized support to areas of ventricular reconstruction or areas of fresh infarction or old scar.

DESCRIPTION OF THE PREFERRED EMBODIMENTS

The present invention is directed to external support of the base of the heart. The support functions to decrease, and/or prevent increases in, the dimensions of the base, and in particular the atrio-ventricular junction, beyond a pre-determined size. The device is designed to reduce the size of the cardiac base in a manner similar to an internal annuloplasty band or ring.

This invention is particularly suited for use in regurgitation of the mitral and tricuspid valves. The device may also be used prophylactically in heart failure surgery to prevent further cardiac basal dilation or expansion even if the underlying mitral and tricuspid valves are competent. The device may be used in moderate or advanced heart failure to prevent progression of basal dilatation or reduce the size of the dilated base.

As used herein, "cardiac base" refers to the junction between the atrial and ventricular chambers of the heart, also known as the atrio-ventricular junction marked externally by the atrio-ventricular groove. This is easily identified in the change of appearance of the cardiac muscle and also the presence of arteries and veins.

The heart is enclosed within a double walled sac known as the pericardium. The inner layer of the pericardial sac is the visceral pericardium or epicardium. The outer layer of the pericardial sac is the parietal pericardium. The term "endocardial surface" refers to the inner walls of the heart. The term "epicardial surface" refers to the outer walls or the heart.

The mitral and tricuspid valves sit at the base of the heart and prevent blood from leaking back into the atria or collecting chambers. See FIG. 1. Mitral regurgitation is a condition whereby blood leaks back through the mitral valve into the left atrium. Over time, this creates a damming of blood in the lungs causing symptoms of shortness of breath. The left heart particularly the left ventricle has to pump a greater volume of blood as a result causing greater strain on this chamber.

Figure 2:
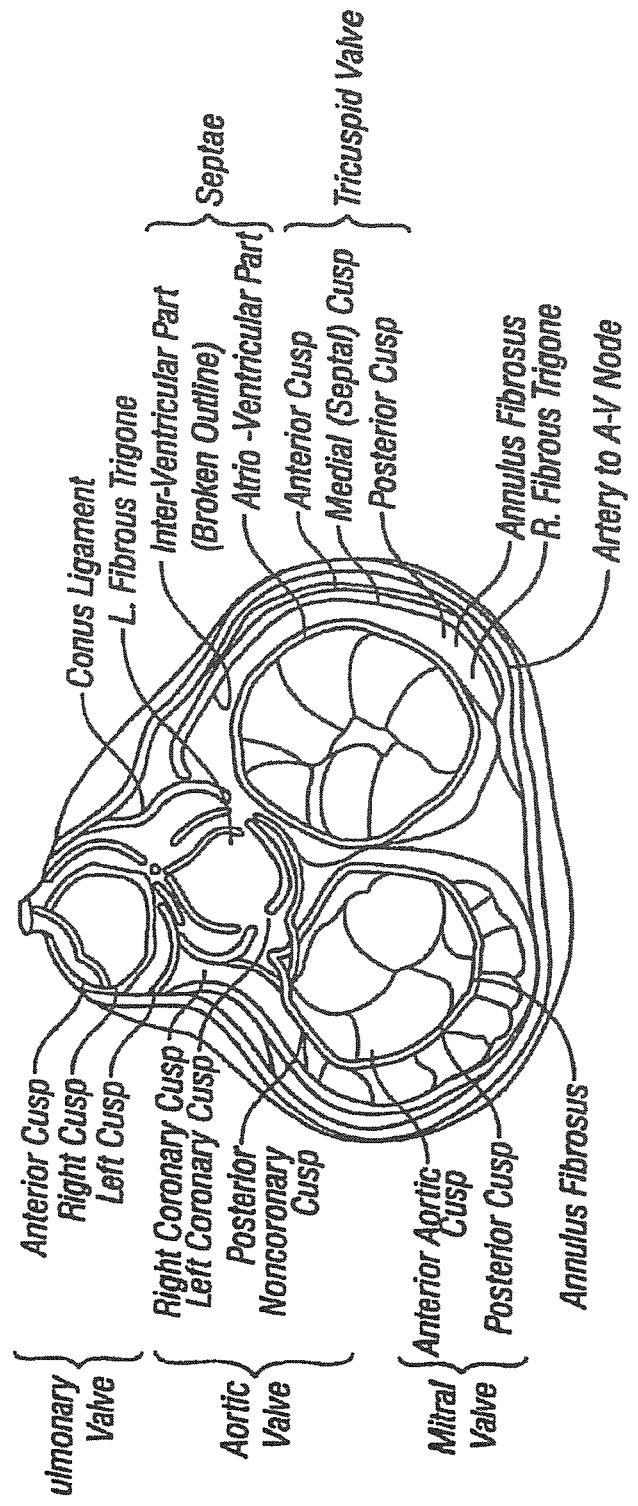
FIG. 2 depicts a cross-section of the base of the heart between the dotted lines depicted in FIG. 1.
Figure 3:
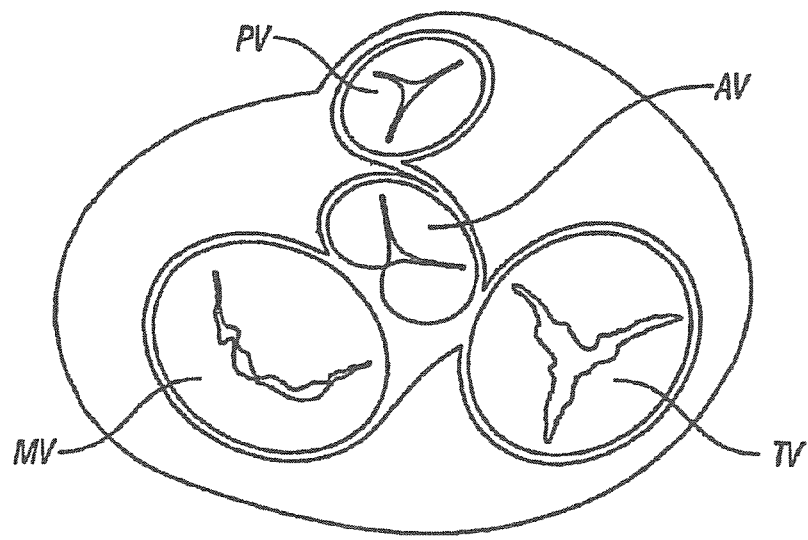
FIG. 3 depicts a cross-sectional schematic diagram of the base of the heart. As depicted therein, PV=pulmonary valve, MV=mitral valve, AV=aortic valve and TV=tricuspid valve.

Dilatation of the mitral annulus occurs maximally in the posterior portion of the annulus, which is not supported by the cardiac fibro-skeleton. FIG. 2 is an anatomic diagram of the base of the heart, showing the valves and the structures in contact with them. FIG. 3 is a schematic representation of the valves at the cardiac base.

Figure 4:
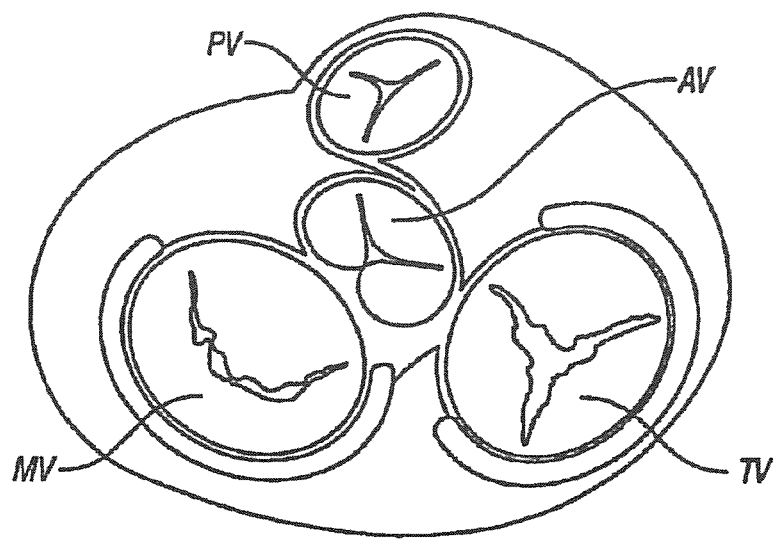
FIG. 4 depicts a traditional method of repairing MV and TV with bands inside the heart.

Mitral valve repair or replacement at present is always performed from inside the heart with the aid of cardiopulmonary bypass. Rings are implanted along the inner surfaces of the entire or expansile portions of the mitral and tricuspid annuli (FIG. 4). Alternatively, when mitral valve malfunction is severe, replacement of the valve with a prosthetic valve may be indicated.

Overview

Figure 5:
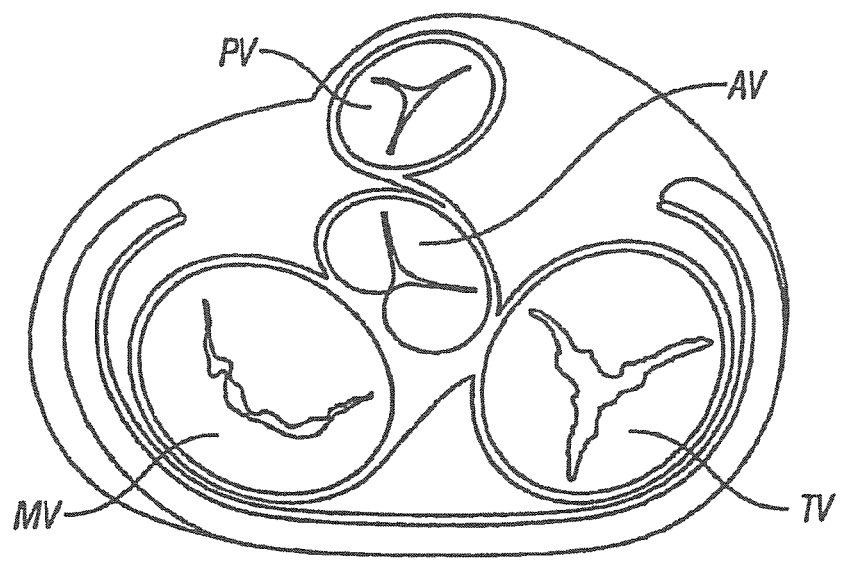
FIG. 5 depicts basal angioplasty of the cardia externally.

The basal ventricular stabilization of the present invention works by using a prosthetic material such as polyester mesh anchored or sutured to the base of the heart at the level of the atrio-ventricular groove. This serves to stabilize the mitral and tricuspid annuli from the outside (FIG. 5). This technique reduces the complexity of the procedure and minimizes the invasive nature and complications from work on the valve. This technique is of particular benefit in patients that have morphologically normal valves with annular dilatation. The device can be applied and anchored to the cardiac base, with the heart beating, without the aid of cardio-pulmonary bypass.

Many patients with moderate degrees of mitral regurgitation are not treated surgically, because the risks of surgery outweigh the potential benefits in this group of patients. However, patients with conditions such as chronic heart failure tend to get very symptomatic even with moderate degrees of mitral regurgitation. These groups of patients would benefit from the less invasive procedures, which are the subject of the present invention. Thus, the potential of this technique in treating mitral regurgitation as a minimally invasive procedure has great appeal as the population ages and more patients manifest with symptoms of heart failure. It also can be applied en passant in patients undergoing coronary artery surgery without the aid of a heart-lung machine.

Device Parameters

The device of the present invention can be constructed of any suitable implantable material. Examples of such materials are well known in the art and include, e.g., synthetic polymers such as polyester, polytetrafluoroethylene, polypropylene, Teflon felt, etc., as well as metallic materials such as stainless steel. Such metals may provide "memory", such that they return to a specific shape after deformation, and in this manner provide an element of dynamic contraction. In yet another embodiment, the device may be constructed either partially or completely by natural materials, such as polyglycolic acid or compressed and/or crosslinked collagen, which may or may not be reinforced with synthetic polymers or other means. Any material is suitable that is biocompatible, implantable, and preferably has a compliance that is lower than the heart wall. Other variations include incorporation of elastic material or elastin ingrowth into the biomaterial.

Figure 6:
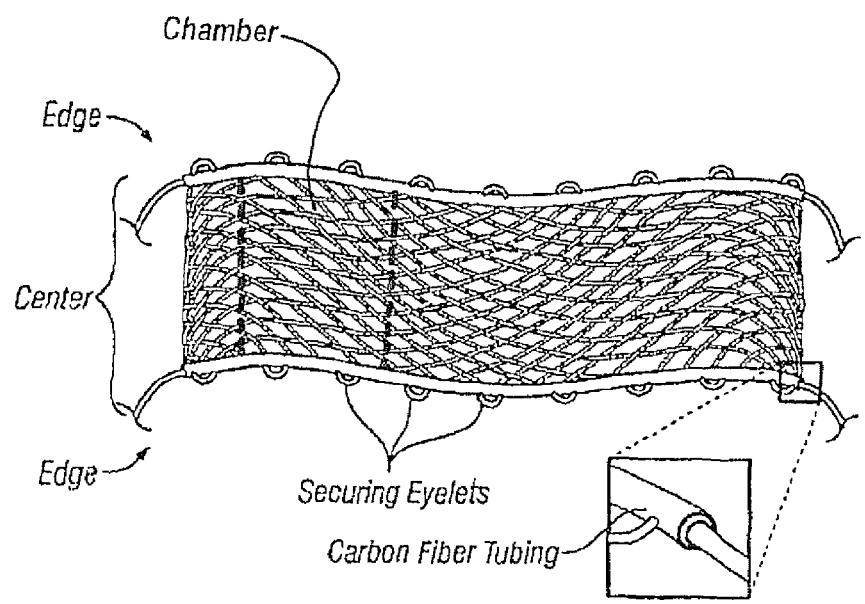
FIG. 6 depicts a representative embodiment of the device of the present invention.
Figure 7:
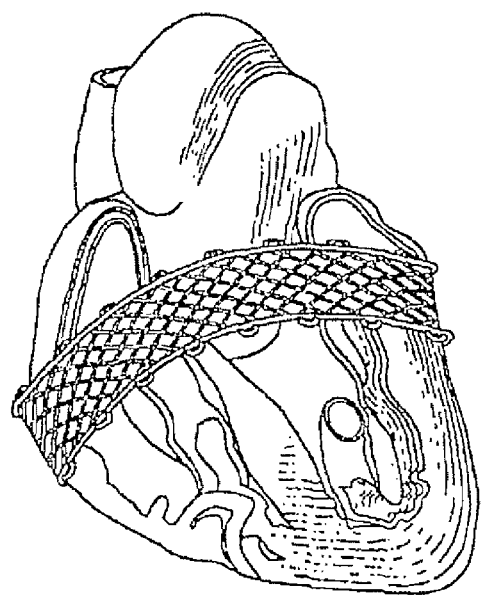
FIG. 7 depicts a schematic drawing of a heart with a representative device in place.

As shown in FIG. 6, the preferred device is in a "strip" configuration and comprised of two edge members and a center portion, each of which may be constructed by the same or different material. In one embodiment (not shown), there is no distinction between the edge members and the center portion and the device is completely uniform from top to bottom.

The center portion of the device may be in the form of a solid single or multi-layer sheet, but is preferably of an open mesh, porous or woven design, such that the exterior of the heart is not completely covered and therefore remains exposed to the surrounding tissue. The size of the openings in the mesh can vary, for example from 2 mm to 2 cm, and can take any shape, such as circular, square, octagonal, triangular, or irregular. In a preferred embodiment, the center portion of the device is a mesh as depicted in FIG. 6.

The center portion may also be adapted for the delivery of various therapeutic agents, such as growth factors or plasma proteins. In addition, it may be adapted to facilitate cellular growth, which in turn may facilitate anchorage of the device.

The device may be designed to completely circle the base of the heart, or it may be a "C" shape, in which case it is specifically designed and implanted so as to not impede blood flow through the aorta and pulmonary artery.

The biomaterial from which the device is constructed may also be radiolucent, radio-opaque or have radio-opaque markers at present intervals to monitor the movement of the cardiac base in real-time using fluoroscopy and to facilitate implantation.

The device may be completely rigid prior to implantation, or may have regions of varying rigidity. However, it is important that the device is sufficiently flexible to move with the expansion and contraction of the heart without impairing its function. It should, however, be designed to prevent expansion of the cardiac base during diastolic filling of the heart to a predetermined size. Since the size expansion parameters of a beating heart are well known, this can be accomplished by testing the device in vitro by applying forces that mimic heart expansion.

The edges of the device, which are depicted in FIG. 6 having securing eyelets attached thereto, may be constructed of a more rigid material, such as carbon fiber tubing. In addition, means of making the device, or portions thereof, such as one or both edges and/or the center portion, more or less rigid post-implantation are also within the present invention. For example, the center portion may be constructed of a partially biodegradable material and may become more flexible-after implantation when the biodegradable material is hydrolyzed by the surrounding tissues and fluids. Alternatively, the edges may be provided with means for making them more rigid or flaccid prior to implantation, such as by inflating/deflating closed chambers. Many alternate means for adjusting the rigidity/flexibility of the device, or portions thereof, would be easily adapted from other mechanisms known in the surgical arts.

Device Attachment

The device may be attached to the outside of the base of the heart by any known method. For example, attachment may be biological, chemical or mechanical. Biological attachment may be brought about by the interaction of the device with the surrounding tissues and cells, and can be promoted by providing appropriate enhancers of tissue growth. Alternatively, chemical attachment may be provided by supplying a mechanism for chemical attachment of the device, or portions thereof, to the external surface of the heart. In yet another embodiment, the rigidity and tightness of the device around the heart may provide for sufficient mechanical attachment due to the forces of the heart against the device without the need for other means of attachment. In a preferred embodiment, however, as depicted in FIG. 6, the device further comprises attachment members, such as the eyelets shown therein. Specific anchor points or loops made of any biocompatible and implantable material may be attached to the edges or to the center portion or both to facilitate anchoring. Suitable materials include, inter alia, polyester, polypropylene or complex polymers. Alternative attachment members may comprise suture materials, protrusions that serve as sites for suturing or stapling, as well as other structural members that facilitate attachment to the surface of the heart.

Device Size

Although the size of the device depends on the purpose for which it is being implanted, it is contemplated that the device will be wide enough (measured from the outside of the first or top edge, i.e. the base edge, to the outside of the second or bottom edge, i.e. the apex edge) to provide efficient support to the atrio-ventricular grove. Accordingly, in one embodiment, the device is between 2 and 5 centimeters wide. In other embodiments, the device may be adapted to provide support over a larger area of the heart. This would provide specifically for reinforcement of areas of scar or muscular weakness as in dyskinetic infracted areas of the myocardium.

Figure 1:
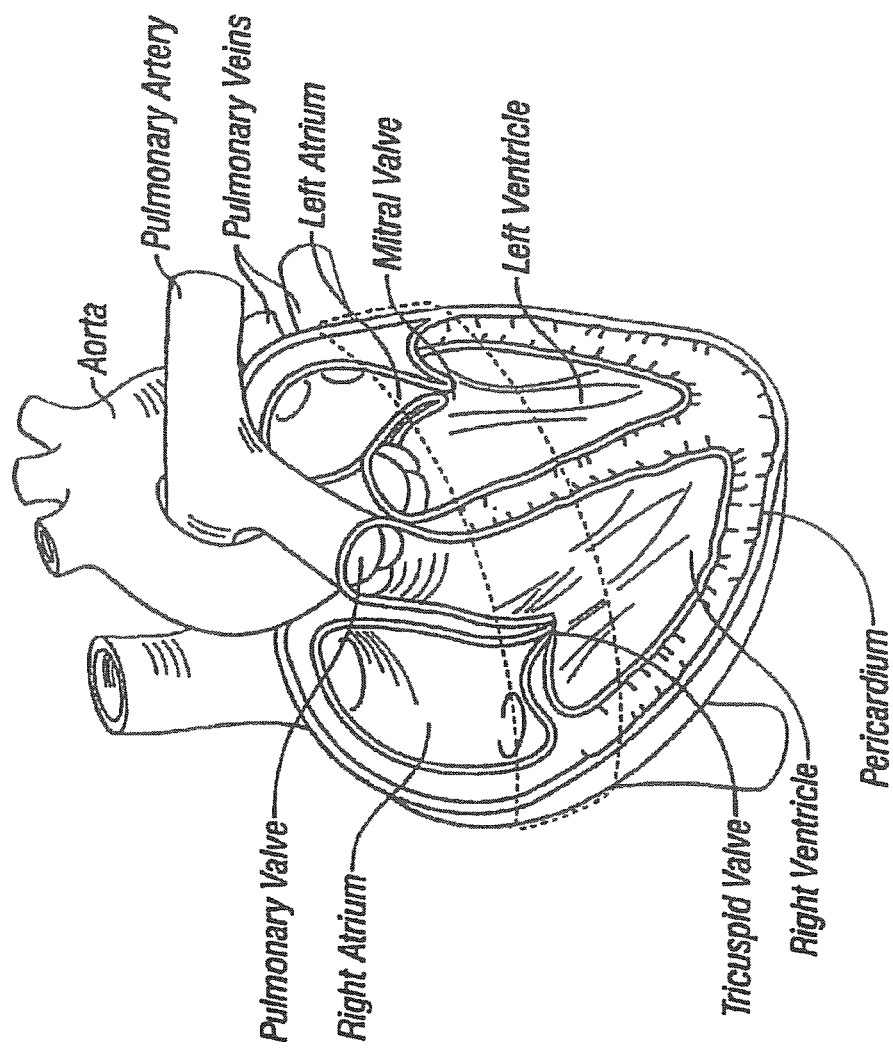
FIG. 1 depicts a cross-section of the heart, showing the approximate location of a representative embodiment of the device of the present invention by dashed lines.

As shown in FIG. 1, the distance between the base and the bottom of the apex of the heart can be expressed as distance "X". Because the focus of the device of the present invention is base stabilization, it is generally preferred that the width of the device be less than or equal to $\frac{1}{2}X$, and be adapted for placement around the top half of the distance X, i.e. closer to the base than the bottom of the apex.

Implantation

The ECBAS or BASE system may be implanted through a conventional midline total sternotomy, sub maximal sternotomy or partial upper or lower sternotomy. Alternatively, the device may be implanted through a thoracotomy incision, or a Video Assisted Thoracoscopic (VAT) approach using small incisions. The BASE system can also be implanted by a sub-costal incision as in the Sub-Costal Hand-Assisted Cardiac Surgery (SHACS). Additionally, the BASE system may be implanted with sutures onto epicardium or clips, staples, or adhesive material that can secure the device on the heart accurately. The device may also be implanted using robotic placement of the device along the posterior aspects of the base of the heart.

The method of implantation and the adequacy of the external annuloplasty can be dynamically assessed by intra-operative trans-esophageal echocardiography, epicardial echocardiography or trans-thoracic echocardiography. The size of the device is assessed based on external circumference measurements of the cardiac base in the fully loaded beating heart state.

Versions of the BACE Systems a. Complete Versus Partial BACE

The ECBAS may completely encircle the cardiac base or just partially support the mitral and tricuspid valve portion of the cardiac base.

b. BACE with Extension

In one embodiment, a limited extension of the ECBAS or a remote patch may be applied to reinforce an area of myocardium that has been reconstructed to exclude an aneurysm or scar.

c. BACE with Pace

In another embodiment, the ECBAS has attached close to or within it epicardial steroid eluting pacing wires that can facilitate multi-site ventricular pacing for heart failure.

d. Dynamic BACE

In this embodiment, the device has fluid filled chambers that may be inflated gradually over time, to gradually reduce the size of the cardiac base. These chambers may also affect passive transfer of energy to facilitate diastolic and systolic support with a closed pericardium.

e. Smart & Dynamic BACE

In this embodiment, the bio-material would have the capability to shrink to a pre-formed size over a period of time, based on the memory of the material or some other programmable characteristic. This would achieve controlled reduction over a period of time of the base of the heart.

f. Cellular BACE

In this embodiment, the bio-material uses available matrix technology, and seeding of appropriate cells to provide dynamic reduction and assistance to the cardiac base.

References

1. Pai R G, Silvet H, Amin J, Padmanabhan S: Prognostic importance of mitral regurgitation at all levels of LV systolic function: Results from a cohort of 8931 patients. *Circulation* 2000; 102(18) Suppl. II: 369.

2. Bolling S F, Pagani F D, Deeb G M. Bach D S: Intermediate-term outcome of mitral reconstruction in cardiomyopathy. *J. Thorac. Cardiovasc. Surg.* 1998; 1 15:381-8.

3. Timek T A, Dagum P, Lai D T, Liang D H, Daughters G T, Ingels N B, Miller D C: Pathogenesis of mitral regurgitation in tachycardia induced cardiomyopathy (TIC). *Circulation* 2000; 102(18) Suppl. II:420.

4. Liel-Cohen N. Guerrero J L, Otsuji Y, Handschumacher M, Rudski L, Hunziker P R, Tanabe H, Scherrer-Crosbie M, Sullivan S, Levine R A: Design of a new surgical approach for ventricular remodeling to relieve ischemic mitral regurgitation: insights from 3-dimensional echocardiography. *Circulation* 2000; 101(23):2756-63.

5. Lamas G A, et al: Poor survival in patients with mild to moderate mitral regurgitation. *Circulation* 1997; 96:827.

EXAMPLES

Example 1

BACE Procedure

Abstract: Over a 12 month period, ten patients underwent Basal Annuloplasty of the Cardia Externally (BACE), to correct moderate mitral regurgitation. This technique involves securing a specially constructed polyester mesh like device to the epicardial surface of the cardiac base, at the level of the atrio-ventricular groove. These procedures were performed in conjunction with coronary artery surgery in all patients. All patients demonstrated a dramatic improvement in functional status, quality of life, mitral regurgitation and function of the heart. BACE can be performed safely with expectation of a good clinical outcome as an adjunct to conventional heart surgery.

Clinical Approach and Experience:

Careful pre-operative screening included radionuclide ventriculography to document left ventricular ejection fraction, a detailed trans-thoracic echocardiogram, a coronary angiogram, and in most cases a stress thallium and/or a Positron Emission Tomographic Scan looking for myocardial viability. The functional statuses of the patients were carefully documented by a heart failure cardiologist and nurse.

Ten patients who were undergoing conventional cardiac surgery, usually in the setting of poor cardiac function with moderate mitral regurgitation, were enrolled. All of these patients had coronary artery bypass surgery. All of them had at least moderate mitral regurgitation pre-operatively and intra-operatively (confirmed by trans-esophageal echocardiography). All of these patients had the Basal Annuloplasty of the Cardia Externally (BACE) performed with a polyester mesh constructed intra-operatively, based on the measured circumference of the cardiac base.

Surgical Technique:

The circumference of the base of the heart at the level of the atrio-ventricular groove was measured before the patient was connected to cardio-pulmonary bypass (CPB). Based on these measurements, a strip of polyester mesh measuring 2.5 to 3 cm in width was cut to size and fashioned, such that its length would be less than the basal circumference by about 2.5 to 4.5 cm. Once the patient was connected to cardiopulmonary bypass, the coronary artery bypass grafts were performed. Left ventricular reconstruction was performed when indicated.

The constructed BACE mesh was anchored posteriorly at the level of the atrio-ventricular groove, on atrial and ventricular sides with combination of 4/0 Ticron™ sutures and hernia staples, which were placed about 1.5 to 2 cm apart. The mesh was secured laterally as well. Final assessment of the tension and the securing of the BACE system was performed with the patient weaned off cardio-pulmonary bypass with the heart filled to pre CPB levels. The mesh was then tightened and secured just as the mitral regurgitation was abolished on trans-esophageal echocardiographic monitoring.

Post-Operative Course:

All these patients had trivial to mild mitral regurgitation at the completion of the procedure. At follow-up, 3, 6 and 12 months post-operatively, all of these patients demonstrated improved cardiac function (as measured by left ventricular ejection fraction), improved functional status and quality of life, and were able to maintain their improvement in the degree of mitral regurgitation. Radionuclide ventriculography was used to determine the left ventricular ejection fraction pre- and post-operatively. Compared to a preoperative value of $25\pm3.1\%$ (n=8), the ejection fractions improved to $40\pm14.2\%$ and $39.3\pm5.7\%$ after 3 and 6 months post-operatively, respectively ($p<5$). Likewise, the New York Heart Association (NYRA) classification was used as an index of functional heart status. Compared to a pre-operative value of $3.11\pm0.33$ (n=8), the NYHA improved to $1.17\pm0.41$ after 3 months post-operatively ($p<5$). Mitral regurgitation (graded 1 to 4) was also observed to improve dramatically from 3.01 pre-operatively to 0.1 post-operatively after 6 months ($p<5$). In addition, there was improvement in tricuspid regurgitation as well.

Discussion: Dilatation of the cardiac base often accompanies heart failure. This may be a secondary development due to volume overload and increased left ventricular wall stress. In cases of mitral or tricuspid valvular heart disease, annular dilatation occurs along with decompensation of the regurgitant lesions. Severe annular dilatation accompanies severe regurgitation. However, significant basal dilatation may co-exist with moderate or moderately severe atrioventricular valve regurgitation. Since repair of these conditions requires intra-cavitary repair of the affected annulus, the majority of surgeons tend to leave moderate and moderately severe mitral and/or tricuspid regurgitation alone. Using the methods and apparatuses of the present invention, these conditions can be corrected from the outside of the heart. Furthermore, the correction can be tailored under trans-esophageal echocardiographic guidance. This avoids intra-cavitary manipulation. In selected cases, this procedure could be performed with heart beating also and without using the heart-lung machine, making it an "off-pump" procedure.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in hematology, surgical science, transfusion medicine, transplantation, or any related fields are intended to be within the scope of the following claims.

Example 2

Comparative and Long Range Studies Using BACE Procedure

Twelve patients were treated with the BACE procedure as described in Example 1. All of the patients had pre- and post-operative studies at 3, 6, 12 and 18 months, including echocardiography and radionuclide ventriculography to look at cardiac function, amount of mitral regurgitation and the size of the hearts. All twelve patients were very symptomatic, with the majority in New York Heart Association (NYHA) class III status. The mean left ventricular ejection fraction (LVEF) was 25% preoperatively and all patients had moderate mitral regurgitation.

The BACE procedure was performed on cardio-pulmonary bypass with the heart decompressed. The procedure took approximately 15 minutes of extra bypass time and about 5 minutes of extra cross-clamp time.

The results are shown below in Table 1. As shown, the BACE procedure dramatically improved cardiac function and was at least equivalent to mitral valve repair eighteen months post-operatively.

TABLE 1

BACE Procedure Results

| | Pre-Op | 6 months | 12 months | 18 months |
| --- | --- | --- | --- | --- |
| NYHA Functional Status | 3.11 | 1.14 | 1.2 | — |
| Left Ventricular Ejection Fraction (%) | 25.0 | 39.3 | 43.1 | 44.5 |
| Degree of Mitral Regurgitation - BACE Patients | 2.8 | — | — | 0.3 |
| Degree of Mitral Regurgitation - Mitral Valve Replacement Patients | 3.7 | — | — | 0.7 |

The invention claimed is:

1. A method of treating a heart disorder, comprising:
    (a) placing a device comprising a biocompatible mesh material, having a predetermined size adapted to encompass a base of a heart, and having at least one chamber attached thereto, around the base of the heart, the biocompatible mesh material having edge portions with attachment members extending therefrom; and
    (b) exerting support on the base of the heart by the chamber after being placed around the base of the heart, wherein the support exertion prohibits an increase of at least a portion of the base of the heart beyond a pre-determined size.

2. The method of claim 1, wherein the at least one chamber is inflatable.

3. The method of claim 1, wherein the at least one chamber is fluid fillable.

4. The method of claim 1, wherein the at least one chamber is fluid filled.

5. The method of claim 1, wherein the mesh material comprises an inner portion and an outer portion, and the at least one chamber is positioned on or contacting the inner portion of mesh material.

6. The method of claim 1, wherein the device is placed in the atrio-ventricular groove of the heart.

7. The method of claim 1, wherein the device is placed along the posterior aspects of the base of the heart.

8. The method of claim 1, wherein the device is placed in the mitral and tricuspid portion of the heart.

9. The method of claim 1, wherein the device stabilizes the mitral and tricuspid annuli of the heart when placed around the heart.

10. The method of claim 1, wherein the at least one chamber increases passive transfer of energy to at least one portion of the base of the heart.

11. The method of claim 1, wherein the exerted support is sufficient to prevent basal dilation during all cardiac cycle phases.

12. The method of claim 1, wherein the exerted support provides a localized increase in contraction at one or more locations of the base.

13. A device for use as an external stabilizer of a heart having a base and an apex, comprising a biocompatible mesh material having a predetermined size adapted to encompass the base of the heart to prevent basal dilation during all cardiac cycle phases heart, the biocompatible mesh material having edge portions with attachment members extending therefrom, and at least one chamber attached to the biocompatible mesh material.

14. The device of claim 13, wherein the at least one chamber is inflatable.

15. The device of claim 13, wherein the at least one chamber is fluid fillable.

16. The device of claim 13, wherein the at least one chamber is fluid filled.

17. The device of claim 13, wherein the mesh material comprises an inner portion and an outer portion, and the at least one chamber is positioned on or contacting the inner portion of the mesh material.

18. The method of claim 1, wherein the attachment members are securing eyelets.

19. The device of claim 13, wherein the attachment members are securing eyelets.

* * * * *